United States Patent [19]
Hodson

[11] Patent Number: 5,469,843
[45] Date of Patent: Nov. 28, 1995

[54] INHALATION DEVICE

[75] Inventor: Peter D. Hodson, Trowell, England

[73] Assignee: Minnesota Mining and Manufacturing Company, St. Paul, Minn.

[21] Appl. No.: 240,675

[22] PCT Filed: Nov. 6, 1992

[86] PCT No.: PCT/US92/09505

§ 371 Date: May 4, 1994

§ 102(e) Date: May 4, 1994

[87] PCT Pub. No.: WO93/09832

PCT Pub. Date: May 27, 1993

[51] Int. Cl.⁶ .................................................. A61M 15/00
[52] U.S. Cl. ................... 128/203.15; 128/203.12; 604/58
[58] Field of Search .................... 604/58; 128/203.12, 128/203.15, 203.21, 203.23

[56] References Cited

U.S. PATENT DOCUMENTS

| | | | |
|---|---|---|---|
| 2,587,215 | 4/1949 | Priestly | 128/206 |
| 2,674,999 | 4/1954 | Cox . | |
| 3,669,113 | 6/1972 | Altounyan et al. | 128/266 |
| 3,948,264 | 4/1976 | Wilke et al. | 128/266 |
| 3,971,377 | 7/1976 | Damani | 128/266 |
| 4,046,146 | 9/1977 | Rosskamp et al. | 128/266 |
| 4,098,273 | 7/1978 | Glenn | 128/206 |
| 4,137,914 | 2/1979 | Wetterlin | 128/203 |
| 4,147,166 | 4/1979 | Hansen | 128/266 |
| 4,192,309 | 3/1980 | Poulsen | 128/203.15 |
| 4,240,418 | 12/1980 | Rosskamp et al. | 128/203.15 |
| 4,667,668 | 5/1987 | Wetterlin | 128/203.15 |
| 4,674,491 | 6/1987 | Brugger et al. | 128/200.14 |
| 4,846,168 | 7/1989 | Abiko et al. | 128/203.15 |
| 4,907,583 | 3/1990 | Wetterlin et al. . | |
| 5,113,855 | 5/1992 | Newhouse | 128/203.15 |
| 5,351,683 | 10/1994 | Chiesi et al. | 128/203.15 |

FOREIGN PATENT DOCUMENTS

| | | | |
|---|---|---|---|
| 0237507 | 9/1987 | European Pat. Off. | A61M 15/00 |
| 1118341 | 7/1968 | United Kingdom | A61M 15/06 |
| 1268051 | 3/1972 | United Kingdom | A61M 15/00 |
| 1478138 | 6/1977 | United Kingdom | A61M 15/00 |
| 1526303 | 9/1978 | United Kingdom | A61M 15/00 |
| 2041763 | 9/1980 | United Kingdom | A61M 15/00 |
| 2061735 | 5/1981 | United Kingdom | A61M 15/00 |
| 2165159 | 10/1985 | United Kingdom | A61M 15/00 |
| 2191718 | 9/1990 | United Kingdom | A61M 15/06 |
| WO90/07351 | 7/1990 | WIPO | A61M 15/00 |
| WO90/13327 | 11/1990 | WIPO | A61M 15/00 |
| 9113646 | 9/1991 | WIPO | 604/58 |
| WO92/08509 | 5/1992 | WIPO | A61M 15/00 |
| 9318811 | 9/1993 | WIPO | 604/58 |

Primary Examiner—Edgar S. Burr
Assistant Examiner—William J. Deane, Jr.
Attorney, Agent, or Firm—Gary L. Griswold; Walter N. Kirn; Dale E. Hulse

[57] ABSTRACT

The present invention relates to a dry powder inhaler having one or more deaglommeration channels through which an airstream containing entrained medicament particles passes. Each channel has a substantially constant cross-sectional area and a bend having a radius of curvature of no greater than 10 mm.

12 Claims, 2 Drawing Sheets

INHALATION DEVICE

FIELD OF THE INVENTION

This invention relates to dry powder inhalation devices.

DESCRIPTION OF THE RELATED ART

Asthma and other respiratory diseases have long been treated by inhalation of medicament. For many years, the two most widely used and convenient choices of treatment have been inhalation of medicament from a drug solution or suspension in an aerosol propellant from a metered dose pressurized inhaler, or inhalation of powdered drug, generally admixed with a powdered excipient, from a dry powder inhaler. With growing concern being voiced over the strong link between depletion of the earth's ozone layer and chlorofluorocarbon emissions, the use of these materials as aerosol propellants in pressurized inhalers is being questioned and interest in dry powder systems has been stimulated.

Most single and multiple dose dry powder inhalers use either individual premeasured doses of medicament which are inserted into a dispensing chamber prior to use, or they incorporate a bulk powder reservoir from which successive quantities of medicament are transferred to the dispensing chamber. Such inhalers generally comprise an air passage leading from the dispensing chamber which terminates in a patient port adapted to be inserted into the mouth or nasal passage of the patient. Patient inhalation at the patient port generates an air stream through the dispensing chamber which carries particles of medicament into the lungs of the patient.

Examples of such dry powder inhalers are disclosed in U.S. Pat. Nos. 2,587,215, 3,669,113, 3,948,264, 3,971,377, 4,046,146, 4,098,273, 4,137,914, 4,147,166, 4,192,309, 4,240,418, 4,674,491, 4,846,168; British Patent Nos. 1,118, 341, 1,268,051, 1,526,303, 2,041,763, 2,061,735, 2,165,159, and 2,191,718; European Patent No. 237507 and International Patent No. WO 90/07351.

A problem common to many dry powder systems is the tendency of the powdered medicament to agglomerate. Agglomeration is caused by individual particles of medicament adhering together in a semi-rigid mass, and requires an increased inspiratory effort by the patient to separate and entrain drug particles into the air stream. If the patient is unable to provide sufficient inspiratory effort the extent of drug penetration into the lower airways of the lung will be reduced. Larger agglomerated drug particles (>10 µm) which result from inefficient aerosolization are not stably entrained into the patient's air stream and prematurely deposit in the mouth or throat region which may lead to unwanted systemic side effects, especially when potent drugs are administered.

It is desirable to utilize the action of the patient's breathing both to deagglomerate and aerosolize the powdered drug, thereby overcoming the coordination problems necessary to synchronize inhalation with means for medicament aerosolization. The efficiency of powder aerosolization, however, is solely determined by the patient's inspiratory effort. Consequently, a patient having difficulty breathing, e.g., during an asthma attack, may possess insufficient inspiratory effort to deagglomerate and aerosolize the medicament and inhale the required dose at a time when the patient has the greatest need for the drug.

Many inhalation devices have attempted to solve the problems attributable to powder agglomeration by incorporating into the device deagglomeration and aerosolization means, e.g., a battery-powered solenoid buzzer, which cause or assist deagglomeration and aerosolization of the powdered medicament by breaking up particle agglomerates entirely independent of the patient's inspiratory effort. Examples of such devices are disclosed in, e.g., U.S. Pat. Nos. 3,948,264, 3,971,377, and 4,147,166. The device may be made fully independent of the patient by incorporating a breath actuation mechanism responsive to respiratory flow, which is able to synchronize medicament release with patient inhalation. An example of such a device is disclosed in our copending International Patent Application No. 90/00670 filed on 30th Apr. 1990.

Dry powder inhalers are also known which incorporate features to assist the break up of particle agglomerates in the powder laden air stream.

For example, British Patent No. 1,268,051 and U.S. Pat. No. 3,669,113 disclose dry powder inhalers in which a premetered dose of powdered medicament is contained in a capsule and the airflow past the capsule is increased in velocity by means of a constriction in the air passage. British Patent No. 2,165,159 discloses a dry powder inhaler with a storage chamber for powdered drug comprising a constricted region in the air passage in the mouthpiece region.

British Patent Nos. 1,478,138, 1,526,303 and 2,061,735 and U.S. Pat. Nos. 3,948,264, 4,046,146, 4,137,914, 4,240, 418, and 4,846,168 disclose dry powder inhalers having an angled mouthpiece which forces the powder laden air stream to pass round a bend.

U.S. Pat. Nos. 2,587,215 and 4,674,491 and International Patent No. WO 90/07351 disclose dry powder inhalers in which the powder laden air stream is forced to take a fairly tortuous path prior to exiting the mouthpieces of the devices. British Patent Nos. 1,118,341 and 2,191,718 and European Patent No. 237507 disclose dry powder inhalers in which the particle laden airstream is forced to pass round interdigitated baffles or similar in the mouthpiece region.

SUMMARY OF THE INVENTION

It has now been found that by providing an air passage for carrying a powder laden airstream with one or more deagglomeration channels of defined configuration, it is possible to impart sufficient shear forces to particle agglomerates entrained therein to separate them into smaller particles which are more readily inhaled by the patient.

Therefore, according to the present invention there is provided a dry powder inhaler for dispensing powdered medicament comprising a housing defining a chamber for receiving a dose of powdered medicament, one or more air inlets, and a patient port adapted for insertion into the mouth or nasal passage of the patient, constructed and arranged to provide an air passage extending from the air inlet(s) through the chamber to the patient port so that patient inhalation at the patient port generates an airflow through the inhaler which entrains particles of medicament from the chamber for inhalation by the patient, and in which the air passage is provided with one or more deagglomeration channels between the chamber and patient through which the airstream with entrained medicament must pass, each channel having a substantially constant cross-sectional profile with a cross-sectional area no greater than 40 $mm^2$, a first opening communicating with the dispensing chamber, a second opening communicating with the patient port and intermediate of said first and second openings either:

(i) a single bend of from 70° to 160° wherein the minimum radius of curvature of the center of the bend is no greater than 10 mm, or (ii) two or more bends each of from 35° to 200°, wherein the minimum radius of curvature of the center of the bends is no greater than 10 mm.

DETAILED DESCRIPTION OF THE INVENTION

The present invention utilizes one or more shaped and dimensioned channels to confine the powder carrying airstream leaving the dispensing chamber, thereby imparting shear and wall friction forces to the particles. These forces are particularly efficient at breaking up particle agglomerates into smaller particles which are capable of being inhaled into the human lung. The cross-sectional profile and dimensions of the deagglomeration channel(s) are selected so as to maximize delivery of respirable sized particles (2 to 5 μm) over the whole range of likely inhalation rates, while minimizing factors such as drug deposition. It has been found that a channel of substantially constant cross-sectional profile of up to 40 mm$^2$ (inclusive), imparts enough shear and wall friction forces to promote the deagglomeration of entrained powder agglomerates.

The final choice of cross-sectional profile will depend on factors such as the starting state of the powder, the required degree of deagglomeration, the pressure drop desired at a particular flow rate and the space available inside the device. The deagglomeration channel(s) may be formed with any suitable profile with the important proviso that the cross-sectional area perpendicular to the longitudinal axis (airflow direction) of the channel is no greater than 40 mm$^2$. It is preferred to avoid shapes with abrupt or angular features which tend to promote excessive powder deposition. Larger channels having a cross-sectional area greater than 40 mm$^2$ tend not to cause adequate deagglomeration of powder. Smaller channels, that is, having a cross-sectional area of less than 40 mm$^2$ aid deagglomeration by increasing air velocities and turbulence, but they also tend to give rise to greater pressure drops for a given airflow rate, resulting in greater powder deposition and therefore a net reduction in the quantity of respirable powder. Thus, it is preferred that the cross-sectional area of the channel(s) is not greater than 30 mm$^2$ and more preferably in the range 15 to 25 mm$^2$.

It is important to ensure that the pressure drop which the patient needs to attain to provide a suitable airflow rate for inhalation of the medicament, typically 30 to 60 liters/minute, is not excessively uncomfortable. A pressure drop of, e.g., ≦400 mm water is suitable.

Each channel incorporates either a single bend of from 70° to 160° or two or more bends, each of from 35° to 180° with the proviso that the radius of curvature of the center of the bend or bends is no greater than 10 mm. The radius of curvature of the center of the bend(s) is preferably no greater than 5 mm and more preferably from 1.5 to 5 mm.

When the channel(s) is formed with two or more bends, then the second and subsequent bends may be formed in the same or in different planes and be of the same or opposing handedness to that preceding it. Preferably, the channel(s) is provided with two bends, with the second bend being of opposing or reverse-handedness to that of the first, thereby forming an 'S' bend. Where the inhaler comprises a plurality of deagglomeration channels they are normally of a similar or identical configuration.

The channel(s) preferably have a uniform cross-sectional profile throughout their length. However, variations in the cross-sectional profile are permitted providing they do not substantially alter the airflow through the channel(s).

Although the deagglomeration channel(s) may be interposed at any suitable point in the air passage between the dispensing chamber and patient port, it is preferred to form the channel(s) in or immediately adjacent to the patient port to avoid excessive pressure drops. Therefore, the space available inside the patient port region of the inhaler is an important factor determining the configuration of the deagglomeration channel(s). This space may be limited in an inhaler incorporating a breath actuation mechanism in the form of a movable vane responsive to patient inspiration. Ideally, the deagglomeration channel(s) should occupy a volume of around 10×15×15 mm.

The overall path length provided by the deagglomeration channel(s), that is, the average distance travelled by the powder laden airstream between the first and second openings, is generally no greater than 4 cm and preferably no greater than 3 cm to avoid excessive powder deposition and pressure drop. The internal surface of the channel(s) may be smooth or it may be patterned, e.g., with grooves angled relative to the direction of the airflow to induce turbulence.

The advantages of the present invention may be summarized as follows:

(a) good deagglomeration performance with a high respirable fraction (typically >35% of the total weight of the powder) and a high respirable dose (e.g., >75 μg);

(b) acceptable pressure drop (e.g., at 60 liters/minute);

(c) small space requirements and ready compatibility with breath actuation mechanisms; and (d) the deagglomeration channel(s) acts as a guard to reduce the chance of any fragments of broken capsules (in capsule dry powder inhalers) or other extraneous matter from being inadvertently inhaled by the patient.

The invention will now be described by way of example with reference to the accompanying drawings in which.

Figure 1:
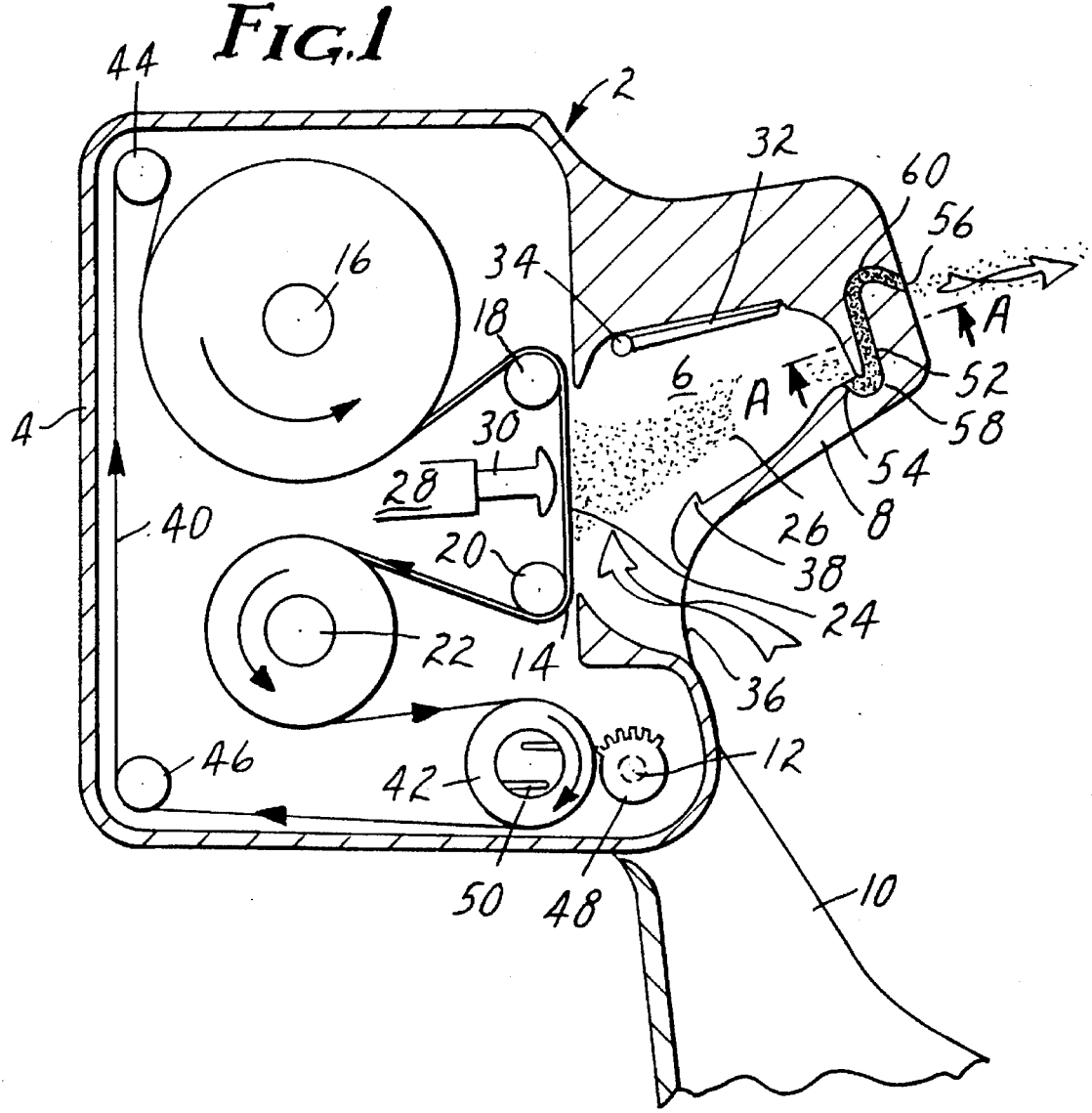
FIG. 1 is a longitudinal section through a dry powder inhaler of the present invention.
Figure 2:
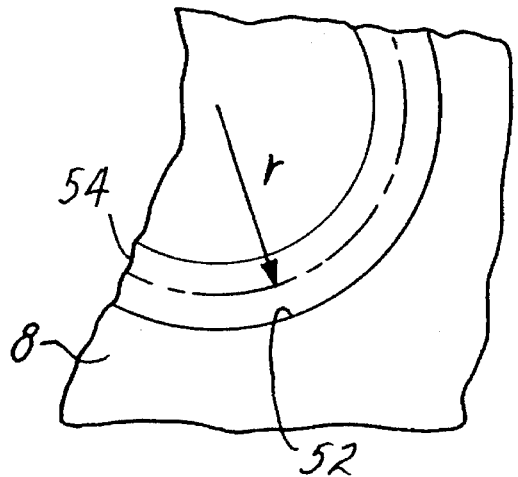
FIG. 2 is an enlarged view of a portion of the mouthpiece of the dry powder inhaler of FIG. 1.
Figure 3:
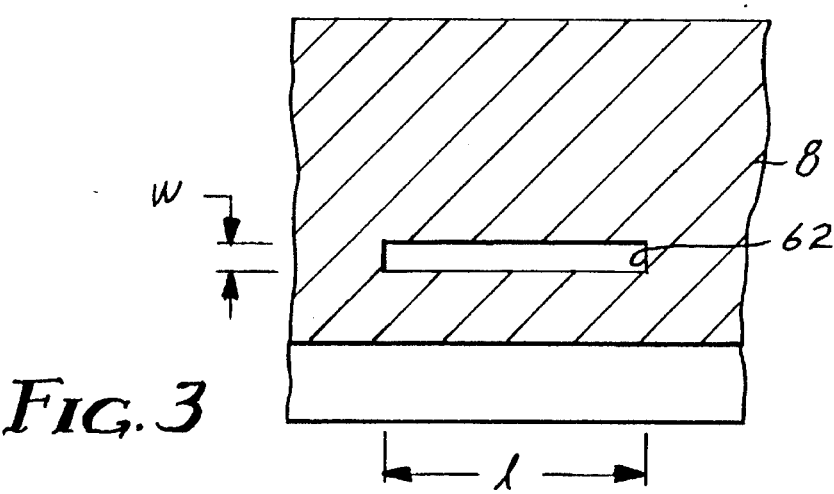
FIG. 3 is a sectional view along the line A—A of the mouthpiece of the dry powder inhaler of FIG. 1, and FIGS. 4 and 5 are sectional views of alternative arrangements of mouthpiece suitable for use with the inhaler of FIG. 1.
Figure 4:
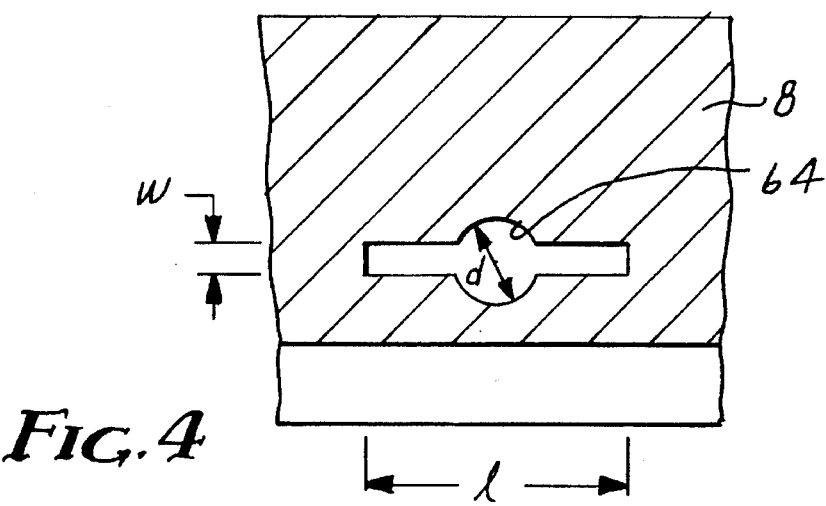
Figure 5:
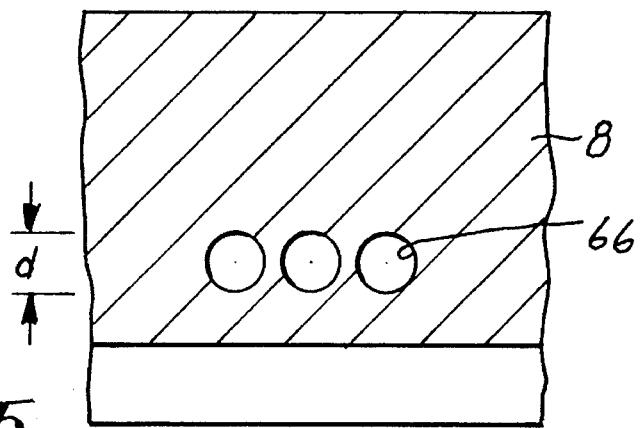

FIG. 1 depicts a dry powder inhaler of the type disclosed in our copending International Patent Application No. GB 90/00670 filed on 30th Apr. 1990. The device (2) comprises a housing (4) defining a dispensing chamber (6) in communication with a patient port in the form of a mouthpiece (8). A cover (10) is movable about pivot point (12) between a closed position (not shown), which protects the contents of the device from the ingress of moisture and other contaminates, and an open, dispensing position as shown.

The housing (4) contains an elongate carrier (14) which is initially wound on a supply spool (16). From the supply spool (16), the elongate carrier (14) passes round two guide rollers (18 and 20) to a take up spool (22). An area (24) of the elongate carrier (14) between the two guide rollers (18 and 20) is exposed to the dispensing chamber (6). When the device (2) is actuated (as shown), powdered medicament (26) is released from the elongate carrier (14) and entrained in the patient's inspiratory airflow.

The device (2) is operated by the patient opening the cover (10) and inhaling through the mouthpiece (8). This activates three mechanisms, namely: a driving mechanism for advancing the elongate carrier (14); an impaction mechanism which causes the exposed area (24) of the elongate carrier (14) to be impacted, thereby ensuring the release of powdered medicament into the patient's airstream, and a trigger mechanism which ensures that the energy stored in the cocked impaction mechanism is not released until inhalation is detected.

The device (2) comprises means to facilitate the release of the powdered medicament (26) from the elongate carrier (14) in the form of an impaction mechanism (28). After the patient-has begun to inhale through the mouthpiece (8), thereby releasing the triggering mechanism, the area (24) of the elongate carrier (14) exposed to the dispensing chamber (6) is struck by a hammer (30) driven by a powerful spring (not shown) to assist the release of medicament (26) into the developing airstream. When cocked, and prior to patient inhalation through the device (2), the hammer (30) is held clear of the elongate carrier (14) by a catch (not shown) which engages the hammer (30) until such time as the trigger mechanism senses patient inhalation. A reset member (not shown) is provided on the cover (10) which, on closure of the device (2), engages and returns the hammer (30) to its original position where it is reengaged by the catch.

The trigger mechanism comprises a movable vane (32) which is pivotally mounted in the mouthpiece (8) at (34) so as to be displaceable when an airflow is generated through the device (2) from the exterior atmosphere to the mouthpiece (8) via air vents (36) (as shown). Displacement of the vane (32) in response to patient inhalation produces an interaction with the catch of the impaction means (28) to release the hammer (30). The vane (32) ensures unidirectional flow of air from the exterior atmosphere to the mouthpiece (8) by being displaceable in the forward direction only. Movement in the reverse direction upon patient exhalation is prevented by stop (38).

The drive mechanism comprises an integral belt (40), the purpose of which is to keep the rotational movement of the supply and take up spools (16 and 22) in precisely the correct relationship to each other and to a control roller (42) regardless of the proportion of the elongate carrier (14) which has been passed between spools. This objective is achieved by the drive belt (40) being in frictional contact with the control roller (42) and with the rear surface of the elongate carrier (14) on each of the spools (16 and 22). In order to achieve the necessary arc of contact between the drive belt (40) and elongate carrier (14) on the spools (16 and 22), the device additionally comprises guide rollers (44 and 46). The elongate carrier (14) is advanced by driving the control roller (42) to cause rotational movement of each spool (16 and 22). The control roller (42) is driven by the act of opening the cover (10) of the device (2) after it has been used by the patient. A drive gear (48) mounted on the pivot (12) of the cover (10) is rotated as the cover (10) is opened and closed. Unidirectional (clockwise) rotation of the control roller (42) is ensured by the provision of a ratchet mechanism (50) which prevents 'wrong-way' rotation when the cover (10) is closed. In this manner, the sequential advancement of unexposed areas (24) of the carrier (14) is coordinated with the simple act of opening and closing the cover (10) of the device (2).

The mouthpiece (8) is provided With a single integrally formed deagglomeration channel (52) which effects the break up of large particle agglomerates released from the carrier (14) into smaller particles of a more respirable size. The deagglomeration channel (52) comprises a first opening (54) communicating with the dispensing chamber (6), a second opening (56) communicating via the mouthpiece with the exterior atmosphere and disposed along its length a first bend (58) of about 150° and a second bend (60) of about 135°. As seen in FIG. 1, bends (58) and (60) are preferably of opposite-handedness so as to form an S shape. Referring by way of example to FIG. 2, which depicts an enlarged view of the first bend (58) of the deagglomeration channel (52), the minimum radius of curvature 'r' of the center of each bend (58 and 60) is no greater than 10 mm, preferably no greater than 5 mm and more preferably between 1.5 and 5 mm (inclusive). It will be appreciated that each bend may not be in the form of a single arc of a circle but may follow a path comprising two or more arcs from circles of different radii conjoined which may include short linear portions. Thus, a bend may follow any desired curve, sinusoidal, parabolic, hyperbolic, etc., providing the other essential parameters of the bend are present. The value of the minimum radius of curvature of the arcs constituting a bend must not be greater than 10 mm. The radius is measured to the centerline of the bend, i.e., mid point between the sidewalls of the channel in the plane of the bend, as shown in FIG. 2.

The deagglomeration channel (52) works by constricting the flow of the powder laden airstream from the dispensing cheer, thereby imparting shear and wall friction forces to the particles entrained therein. It is these forces which are responsible for the breakup of the particle agglomerates. Although the deagglomeration channel may have any suitable cross-section which does not promote excessive powder deposition, three particularly preferred profiles are illustrated in FIGS. 3, 4, and 5. In each case, the total cross-sectional area of the channel when measured at a point perpendicular to the longitudinal axis of the channel should not exceed 40 $mm^2$ and is preferably no more than 30 $mm^2$.

Referring to FIG. 3, the deagglomerator channel is formed with a slot (rectangular) or bar-shaped profile or cross-section (62) typically having a length (l) of from 8 to 40 mm, preferably 8 to 30 mm and more preferably 8 to 16 mm and a width (w) of from 1 to 5 mm, preferably 1 to 2.5 mm and more preferably 1.2 to 1.6 mm. A slot of 14 mm length with a width of 1.5 mm (total cross-section 21 $mm^2$) was found to release doses of 180 μm, from an inhaler of the type shown in FIG. 1 with about 70 μm (39%) of the particles having a size in the range of from 2 to 5 μm (as recorded using a twin stage impinger at a flow rate of 60 l/min).

FIG. 4 shows a modification to the deagglomeration channel of FIG. 3, in which an opening or enlarged portion (64) of greater dimension is formed along the center of the channel in order to reduce the pressure drop experienced by the patient, particularly at high inhalation rates, by providing a central, lower resistance, less turbulent bypass route for air at high flow rates. However, the majority of the powder aerosol still passes close to the walls of the channel where the deagglomerating forces are at their strongest. Typical values for 'l', 'w', and 'd' are 14, 1.5, and 4 mm respectively.

FIG. 5 illustrates a further arrangement of mouthpiece where the single slot or modified slot of FIGS. 3 and 4 have been replaced by three equi-size channels of circular cross-section (66). The diameter 'd' of each channel is generally in the range of from 2 to 7 mm, preferably 2 to 5 mm with a typical value of about 3 mm.

I claim:

1. A dry powder inhaler for dispensing powdered medicament, comprising a housing defining a chamber for receiving a dose of powdered medicament, one or more air inlets, and a patient port adapted for insertion into the mouth or nasal passage of the patient, said housing being constructed and arranged to provide an air passage extending from the air inlet(s) through the chamber to the patient port so that patient inhalation at the patient port generates an airstream through the inhaler which entrains particles of medicament from the chamber for inhalation by the patient, the air passage being provided with one or more deagglomeration channels between the chamber and patient port through which the airstream with entrained medicament must pass, each channel having a substantially constant cross-sectional profile with a cross-sectional area no greater than 40 mm², a first opening communicating with the chamber, a second opening communicating with the patient port, and adjacent said first opening a first bend of 35° to 200° and adjacent said second opening a second bend of 35° to 200°, wherein the minimum radius of curvature of the center of each of the first and second bends is no greater than 10 mm, said first and second bends being of opposite-handedness so as to form an S shape.

2. A dry powder inhaler as claimed in claim 1 in which the one or more deagglomeration channel(s) has a cross-sectional area no greater than 30 mm².

3. A dry powder inhaler as claimed in claim 1 in which the one or more deagglomeration channel(s) has a cross-sectional area of from 15 to 25 mm².

4. A dry powder inhaler as claimed in claim 1 in which the minimum radius of curvature of the center of each of the first and second bends is no greater than 5 mm.

5. A dry powder inhaler as claimed in claim 4 in which the minimum radius of curvature of the center of each of the first and second bends is from 1.5 to 5 mm.

6. A dry powder inhaler as claimed in claim 1 wherein the first bend is about 150° and the second bend is about 135°.

7. A dry powder inhaler as claimed in claim 1 in which the overall path length between the first and second openings of the one or more deagglomeration channel(s) is no greater than 4 cm.

8. A dry powder inhaler as claimed in claim 1 in which the one or more deagglomeration channel(s) has a rectangular cross-section of length 8 to 30 mm and width 1 to 2.5 mm.

9. A dry powder inhaler as claimed in claim 1 in which the one or more deagglomeration channel(s) has a rectangular cross-section of length 8 to 16 mm and width 1.2 to 1.6 mm.

10. A dry powder inhaler as claimed in claim 8 wherein the one or more deagglomeration channel(s) has an enlarged portion formed along the center thereof.

11. A dry powder inhaler as claimed in claim 1 in which the one or more deagglomeration channel(s) has a circular cross-section of diameter 2 to 7 mm.

12. A dry powder inhaler as claimed in claim 1 in which the one or more deagglomeration channel(s) is formed in the patient port.

* * * * *